United States Patent [19]

Carter et al.

[11] Patent Number: 5,266,722

[45] Date of Patent: Nov. 30, 1993

[54] POLYETHER BIS-PHOSPHONIC ACID COMPOUNDS

[75] Inventors: Charles G. Carter, Silver Springs; Ranjit Kumar, Columbia, both of Md.

[73] Assignee: W. R. Grace & Co.-Conn., New York, N.Y.

[21] Appl. No.: 269,205

[22] Filed: Nov. 9, 1988

[51] Int. Cl.$^5$ .............................. C07F 9/38; C07F 9/40
[52] U.S. Cl. ................................... 562/20; 558/155; 558/163; 558/165; 558/184; 558/186; 558/189; 562/23
[58] Field of Search ................... 558/155, 163, 165; 562/20

[56] References Cited

U.S. PATENT DOCUMENTS

| | | | |
|---|---|---|---|
| 2,535,172 | 12/1950 | Tawney | 558/183 |
| 2,632,767 | 3/1953 | Smith et al. | 558/164 |
| 2,900,408 | 8/1959 | Blaser et al. | 558/116 |
| 3,032,578 | 5/1962 | MacMullen et al. | 558/186 |
| 3,341,467 | 9/1967 | Hwa | 252/321 |
| 3,429,824 | 2/1969 | Tate | 252/180 |
| 3,488,289 | 1/1970 | Tate | 252/180 |

(List continued on next page.)

FOREIGN PATENT DOCUMENTS 535946 1/1957 Canada .
2112370A 7/1983 United Kingdom .

OTHER PUBLICATIONS

*Advanced Organic Chemistry* by Jerry March (3rd Ed.) pp. 239, 310 (1985).

(List continued on next page.)

Primary Examiner—Emily Bernhardt
Attorney, Agent, or Firm—James P. Barr

[57] ABSTRACT

Polyether bis-phosphonic acid compounds are disclosed which have the formula $(HO)_2OP-R-(OR'-)_n-OR-PO(OH)_2$ where R is selected from the group consisting of methylene and ethylene, R' is selected from the group consisting of ethylene and ethylene substituted with one or more methyl groups, and n is an integer from 1 to 4, water soluble salts thereof, and esters thereof with alkyl groups having from 1 to 6 carbon atoms. Also disclosed is a novel preparation of certain of these compounds by reacting certain hydroxyalkylphosphonic acid dialkyl ester compounds with certain 2-benzyloxyalkyl organic sulfonates; reacting the intermediate formed therefrom with hydrogen or a hydrogen source; reacting the intermediate formed therefrom with a hydrogen ion acceptor and certain sulfonyl chlorides; and reacting the intermediate formed therefrom with certain hydroxyalkyl-phosphonic acid dialkyl ester compounds to form a polyether bis-phosphonic acid compound which may be hydrolyzed to form the polyether bis-phosphonic acid. Useful intermediates are disclosed which have the formulas

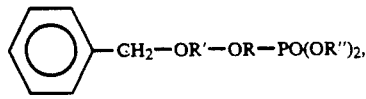

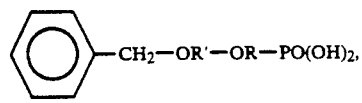

$HOR'-OR-PO(OR'')_2$, $HOR'-OR-PO(OH)_2$, and $X-O_2S-OR'-OR-PO(OR'')_2$, wherein the above-indicated benzene rings of said formulas are optionally substituted with selected groups, wherein R and R' are as defined above, wherein R" is an alkyl group having from 1 to 6 carbon atoms, and wherein X is selected from

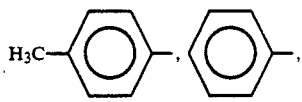

and alkyl groups having from about 1 to 6 carbon atoms.

6 Claims, No Drawings

U.S. PATENT DOCUMENTS

| | | | |
|---|---|---|---|
| 3,510,436 | 5/1970 | Silverstein et al. | 252/389 |
| 3,532,639 | 10/1970 | Hatch | 252/389 |
| 3,600,470 | 8/1971 | Lewis | 558/124 |
| 3,714,066 | 1/1973 | King et al. | 252/389 A |
| 3,738,806 | 6/1973 | Feiler | 21/27 |
| 3,803,047 | 4/1974 | Hwa | 252/389 A |
| 3,803,048 | 4/1974 | Hwa | 252/389 A |
| 3,837,803 | 9/1974 | Carter et al. | 252/389 A |
| 3,890,228 | 6/1975 | Hwa et al. | 252/180 |
| 3,960,576 | 6/1976 | Carter et al. | 252/389 A |
| 3,970,729 | 7/1976 | Walsh et al. | 558/104 |
| 4,003,842 | 1/1977 | Suen et al. | 252/175 |
| 4,029,696 | 6/1977 | Sommer et al. | 260/502.5 |
| 4,052,160 | 10/1977 | Cook et al. | 106/14 |
| 4,056,480 | 11/1977 | Herber | 252/78.5 |
| 4,067,931 | 1/1978 | Batorewicz | 558/165 |
| 4,069,247 | 1/1978 | Kleiner | 260/502.4 R |
| 4,085,134 | 4/1978 | Redmore et al. | 260/502.5 |
| 4,092,244 | 5/1978 | Suen et al. | 252/180 |
| 4,206,075 | 6/1980 | Boffardi | 252/389 A |
| 4,209,487 | 6/1980 | Hogue et al. | 422/12 |
| 4,212,832 | 7/1980 | Mitschke et al. | 558/165 |
| 4,276,089 | 6/1981 | Moran | 106/14.12 |
| 4,416,830 | 11/1983 | Morr et al. | 558/164 |
| 4,440,646 | 4/1974 | Budnick | 266/502.4 R |
| 4,465,516 | 8/1984 | Danner et al. | 106/14.12 |
| 4,631,142 | 12/1986 | Sturtz | 252/184 |
| 4,717,542 | 1/1988 | Mitchell | 422/15 |
| 4,719,031 | 1/1988 | Coleman | 260/545 P |
| 4,911,887 | 3/1990 | Carter | 422/15 |

OTHER PUBLICATIONS

Wadsworth et al, *JACS* 83 p. 1753 (1961).
Bunnett et al, *JACS* 72 p. 2378 (1952).
Buehler et al, "Survey of Organic Syntheses", (1974) p. 290.
McOmie, "Protective Groups in Organic Chemistry", (1973) pp. 98-100.
Wagner et al. "Synthetic Organic Chemistry", (1953) p. 823.
Garifzyanov et al., *Chemical Abstracts*, vol. 110, No. 83099 (for Izv.Vyssh.Uchebn.Zaved.Khim.Khim.-Tekhnol, 31, p. 75 Sep. 1988).
L. Maier et al. "Organic Phosphorus Compounds. 70. Preparation and Properties of New Phosphorus Containing Chelating Agents for Calcium and Magnesium Ions", Phosphorous and Sulfur, 5, 45-51 (1978).
Chem. Abstracts, vol. 96, entry 183846E (1982); Stulli et al.: "Effect of Complexing Agents on the Properties of Synthetic Cutting Fluids" Khim. Tekhnol. Topl. Masel.
Chem. Abstracts vol. 95, entry 61756j (1981)-Jupe et al. "Polyhydric Phenols Ger. Offen. 2,942,366".
D. A. Nicholson et al. "A Convenient Method of Esterification of Polyphosphonic Acids", Journal of Organic Chemistry, 35, 3149-3150 (1970).
K. A. Petrov et al. "Synthesis and Properties of (Substituted Methyl) Phosphonates" Zhur. Obschchei. Khim. 12 2741-9 (1977) (1978 Translation Plenum Publishing Corp. 2494-2501).
D. P. Phillion et al. "Synthesis and Reactivity of Diethyl Phosphonomethyltriflate" Tet. Lett. 27 1477-1480 (1986).
D. Redmore "Heterocuclic Systems Bearing Phosphorus Substituents. Synthesis and Chemistry", Chem. Rev., 71, 315-337 (1971) and Table III.
J. S. Amato et al. "A New Preparation of Chloromethyl Methyl Ether Free of Bis(chloromethyl) Ether", Synthesis 970-971 (1979).
T. H. Chan et al. "Unexpected Site Selectivity of Halotrimethylsilane with 2,5-Dimethoxytetrahydrofuran and 2,6-Dimethoxytetrahydropyran" Tet Lett. 24 1225-1228 (1983).
Griffiths et al. "The Reaction of Phosphorus Trichloride and Paraformaldehyde" Phosphorous, 6, 223-230 (1976).
Chemical Abstracts vol. 58, Cols. 6866-6868 (1963) S. Julia et al. "Synthesis of Substituted-and-Cchlohomocitrals and the Corresponding Ketones and Alcohols" Bull Soc. Chim. Grance, 1952-1959 (1962).
Stauffer Chemical Company, Flame Retardant Chemical Product Data-Hydroxymethyl Phosphonic Acid. (1966).
Stauffer Chemical Company, Material Safety Data Sheet, Hydroxymethylphosphonic Acid. (1960).
Chemical Abstracts vol. 37, Cols. 3048-3049 (1943) V. S. Abramov et al. "Action of Dibromomethyl and Dichloromethyl Ethers on Ethyl Phosphite and Sodium Diethyl Phosphite".
Chemical Abstracts, vol. 55, Col. 6367 (1961), K. A. Petrov et al.
"Diphosphonates. III. Synthesis of O- and S-Diphosphonates" Zhur. Obshchei Khim. 30, 1960-4 (1960).
Chemical Abstracts, vol. 56, Cols. 11418-11419 (1962), W. Treibs et al. "Autooxidation in the Presence of Alcohols and Protons III. Autooxidation of Cyclenes, Hydroarenes, and Hydrocheterocycles" Chem. Ber. 94 2983-2989 (1961).

POLYETHER BIS-PHOSPHONIC ACID COMPOUNDS

FIELD OF THE INVENTION

This invention relates to a novel class of phosphonic acid compounds useful in water treatment and to the preparation of those compounds, and more particularly to a class of polyether bis-phosphonic acid compounds, certain of their precursors and certain derivatives of those precursors, as well as to the preparation thereof from dialkyl hydroxyalkylphosphonic acid esters.

BACKGROUND

Much recent research has concerned development of organic corrosion inhibitors which can reduce reliance on the traditional inorganic inhibitors. Among the organic inhibitors successfully employed are numerous organic phosphonates. These compounds may generally be used without detrimental interference from other conventional water treatment additives. Hydroxymethylphosphonic acid has been reported as useful in combination with zinc for corrosion control.

Phosphonic acid compounds have also been used in other fields for such purposes as flame retardants, plasticizers, lubricants, and surfactants. U.S. Pat. No. 3,032,578 discloses for example certain aryloxypolyakylene ether phosphonates which exhibit useful properties as surface active agents, and are prepared by reacting a trialkyl phosphite with an aryloxypolyalkylene ether halide to form the corresponding dialkyl phosphonate, which is then hydrolyzed to the corresponding phosphonic acid.

SUMMARY OF THE INVENTION

This invention relates to a novel class of polyether bis-phosphonic acid compounds, certain of their precursors, and certain derivatives of those precursors. We have found that certain bis-phosphonic acid compounds may be prepared by a method which comprises the steps of (a) reacting (i) a hydroxyalkylphosphonic acid dialkyl ester compound of the formula MOR—PO(OR")$_2$ where R is methylene or ethylene, R" is an alkyl group having from 1 to 6 carbons, and M is an alkali metal or an alkaline earth metal, with (ii) a compound selected from the group consisting of 2-benzyloxyalkyl p-toluenesulfonate, 2-benzyloxyalkyl benzenesulfonate and 2-benzyloxyalkyl alkylsulfonate to form a first intermediate, the alkyl group of said alkylsulfonate having from about 1 to 6 carbon atoms, the oxyalkyl group of said sulfonate corresponding to the formula OR' where R' is selected from the group consisting of —CH$_2$CH$_2$—, and —CH$_2$CH$_2$— which is substituted with one or more methyl groups, and the benzene ring of the benzyl group of said sulfonate being optionally substituted with one or more substituents selected from the group consisting of halogen groups, alkyl groups having from 1 to 30 carbon atoms and alkoxy groups having from about 1 to 30 carbon atoms; (b) reacting said first intermediate with hydrogen or a hydrogen source to form a second intermediate; (c) reacting said second intermediate with a hydrogen ion acceptor and a compound selected from the group consisting of toluene sulfonyl chloride, benzene sulfonyl chloride, and alkane sulfonyl chlorides having from 1 to about 6 carbon atoms to form a third intermediate; and (d) reacting said third intermediate with a hydroxyalkylphosphonic acid dialkyl ester compound of the formula MOR—PO-(OR")$_2$, where R, R" and M are as recited above. The reaction product of step (d) may then be hydrolyzed to form a polyether bis-phosphonic acid. These and other novel polyether bis-phosphonic acid compounds of the formula

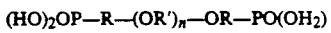

(HO)$_2$OP—R—(OR')$_n$—OR—PO(OH$_2$)

where R is selected from the group consisting of —CH$_2$— and —CH$_2$CH$_2$—, R' is selected from the group consisting of —CH$_2$CH$_2$—, and —CH$_2$CH$_2$— which is substituted with one or more methyl groups, and n is an integer from 1 to 4, as well as water soluble salts thereof and esters thereof with alkyl groups having from 1 to 6 carbon atoms are provided in accordance with this invention. Certain precursors of these bis-phosphonic acid compounds, and derivatives of those precursors, are also provided in accordance with this invention especially those corresponding to the formulas

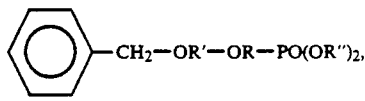

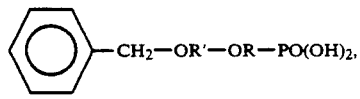

HOR'—OR—PO(OR")$_2$, HOR'—OR—PO(OH)$_2$, and their water salts, where R, R', and R" are as recited above and the benzene rings are optionally substituted with one or more substituents selected from the group consisting of halogen groups, alkyl groups having from about 1 to 30 carbon atoms, and alkoxy groups having from about 1 to 30 carbon atoms; as well as those corresponding to the formula X—O$_2$S—OR-'—OR—PO(OR")$_2$ where R, R' and R" are as recited above and X is selected from the group consisting of

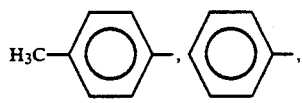

and alkyl groups having from about 1 to 6 carbon atoms.

It is an object of this invention to provide new and useful phosphonic acid compounds.

It is another object of this invention to provide a novel method of preparing certain of these compounds.

These and other objects of this invention will become apparent from the detailed description which follows.

DETAILED DESCRIPTION

This invention relates to novel polyether bis-phosphonic acid compounds having the general formula

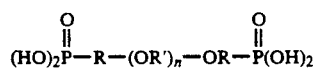

(HO)$_2$P—R—(OR')$_n$—OR—P(OH)$_2$ where R is selected from the group consisting of methylene (i.e. —CH$_2$—) and ethylene (i.e. —CH$_2$CH$_2$—), R' is selected from the group consisting of ethylene, and ethylene substituted with one or more methyl groups (e.g. —CH$_2$C(CH$_3$)H—), and n is an integer from 1 to 4, water soluble salts thereof, and esters thereof with alkyl groups having from 1 to 6 carbons. A preferred group of these compounds for water treatment includes the polyether bis-phosphonic acids and their water soluble salts. Alkali metal salts of these compounds are considered particularly useful for corrosion control applications.

The polyether bis-phosphonic acid compounds of this invention can be prepared from the hydroxymethylphosphonic acid dialkyl ester salts and hydroxyethylphosphonic acid dialkyl ester salts having the formula:

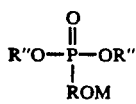

where R is as described above, R" is an alkyl group having from 1 to 6 carbons, preferably methyl or ethyl, and M is an alkali metal or an alkaline earth metal, preferably sodium or potassium.

A method of preparing the polyether bis-phosphonic acid compounds of this invention where n is equal to 1 includes the steps of: (a) reacting (i) the hydroxyalkylphosphonic acid dialkyl ester compound of the above-referenced formula with (ii) 2-benzyloxyalkyl p-toluenesulfonate to form a first intermediate, the oxyalkyl group of said toluenesulfonate corresponding to the formula OR' where R' is as described above for the polyether bis-phosphonic acid compounds of this invention; (b) reacting said first intermediate with hydrogen or a hydrogen source such as cyclohexene in the presence of palladium on carbon to form a second intermediate; (c) reacting said second intermediate with toluene sulfonyl chloride and a suitable hydrogen ion acceptor such as pyridine, substituted pyridines or trialkyl amines to form a third intermediate; and (d) reacting said third intermediate with a hydroxyalkylphosphonic acid dialkyl ester compound of the above-referenced formula to form tetraalkyl alkyleneglycol di-(phosphonoalkyl) ether. The reaction product of step (d) (i.e. the tetraalkyl alkyleneglycol di-(phosphono-alkyl) ether) may then be hydrolyzed to yield the corresponding alkyleneglycol di-(phosphonoalkyl) ether.

The hydroxyalkylphosphonic acid dialkyl ester salts of the above-referenced formula may be produced from the corresponding hydroxyalkylphosphonic acid dialkyl ester during preparation. Thus, step (a) is suitably accomplished by adding a solution of the toluenesulfonate and either hydroxymethylphosphonic acid dialkyl ester or hydroxyethylphosphonic acid dialkyl ester, as appropriate, in a solvent such as ethylene glycol dimethyl ether to a slurry of sodium hydride in said solvent under an inert atmosphere such as nitrogen or argon. Step (b) is suitably accomplished by dissolving the first intermediate together with cyclohexene a solvent such as ethanol; adding palladium on carbon to the solution and heating the resulting slurry under an inert atmosphere such as nitrogen or argon to reflux. Step (c) is suitably accomplished by dissolving the second intermediate in a solvent such as dichloromethane under an inert atmosphere such as nitrogen or argon; adding toluene sulfonyl chloride to the solution, and adding a solution of pyridine in said solvent to the mixture. Step (d) is suitably accomplished by dissolving the third intermediate together with either hydroxymethylphosphonic acid dialkyl ester or hydroxyethylphosphonic acid dialkyl ester, as appropriate, in a solvent such as ethylene glycol dimethyl ether and adding the solution to a slurry of sodium hydride in said solvent under an inert atmosphere such as nitrogen or argon. The alkylene glycol di-(phosphonoalkyl) ether may be produced by dissolving the tetraalkyl alkyleneglycol di-(phosphonoalkyl) ether in a concentrated acid, such as hydrochloric acid and refluxing the acid solution.

Accordingly, the compound

(i.e., each R is methylene, R' is ethylene, and n is 1) may be conveniently prepared by: (a) adding a solution of (i) the diethyl ester of hydroxymethylphosphonic acid and (ii) 2-benzyloxyethyl p-toluene sulfonate in ethylene glycol dimethyl ether to a slurry of sodium hydride in ethylene glycol dimethyl ether under a nitrogen atmosphere, thereby forming diethyl 2-(benzyloxy)ethoxymethylphosphonate as a first intermediate; (b) (i) dissolving the first intermediate together with cyclohexene in ethanol; and (ii) adding paladium on carbon to the solution of step (b)(i) and heating the resulting slurry under nitrogen to reflux, thereby forming diethyl 2-hydroxyethoxymethylphosphonate as a second intermediate; (c) (i) dissolving said second intermediate in dichloromethane under a nitrogen atmosphere; (ii) adding toluene sulfonyl chloride to the solution of step (c) (i); and (iii) adding a solution of pyridine in dichloromethane to the mixture of step (c) (ii) thereby forming diethyl 2-(phosphonomethoxy)ethyl p-toluene sulfonate as a third intermediate; (d) (i) dissolving said third intermediate together with the diethyl ester of hydroxymethylphosphonic acid in ethylene glycol dimethyl ether; and (ii) adding the solution of step (d) (i) to a slurry of sodium hydride in ethylene glycol dimethyl ether under a nitrogen atmosphere, thereby forming tetraethyl ethyleneglycol di-(phosphonomethyl) ether. The tetraethyl ethyleneglycol di-(phosphonomethyl) ether may be disssolved in concentrated hydrochloric acid and the resulting solution refluxed to yield ethylene-glycol di-(phosphonomethyl) ether.

We prefer to substantially purify the first intermediate produced in step (a) before proceeding to step (b). This may generally be accomplished for example by silica gel chomatography. The first intermediate as described above comprises compounds corresponding to the formula:

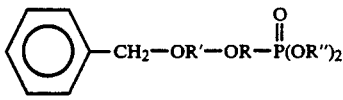

Moreover, it is considered that the benzene ring of the 2-benzyloxyalkyl compound used in step (a) above can be optionally substituted with one or more substituents selected from the group consisting of halogen groups, alkyl groups, and alkoxy groups, said alkyl and alkoxy groups having from 1 to about 30 carbon atoms. Accordingly the benzene ring of the first intermediate may be correspondingly substituted. In addition to their utility in the production of the polyether bis-phosphonic acid compounds of this invention, these first intermediate esters can themselves be hydrolyzed by conventional means to the corresponding phosphonic acids and water soluble salts thereof, which are considered useful in water treatment (e.g. as corrosion or scale inhibitors) and, especially for embodiments where the benzene is substituted with the longer chain substituents, surfactants.

We prefer to isolate the second intermediate produced in step (b) before proceeding to step (c). This may generally be accomplished for example by removing the catalyst by filtration and concentrating the filtered solution under vacuum.. The second intermediate as described above comprises compounds corresponding to the formula:

In addition to their utility in the production of the polyether bis-phosphonic acid compounds of this invention, these second intermediate esters can themselves be hydrolyzed by conventional means to the corresponding phosphonic acids, and water soluble salts thereof, which are considered useful in water treatment as corrosion and/or scale inhibitors.

We prefer to substantially purify the third intermediate produced in step (c). This may generally be accomplished for example by silica gel chromatography. The third intermediate as described above comprises compounds corresponding to the formula:

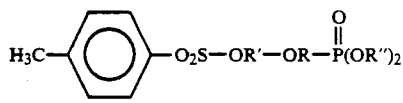

Moreover it is considered that the toluene sulfonyl chloride used in step (c) above can be replaced with other reactants such as alkane sulfonyl chlorides having from about 1 to 6 carbon atoms, and benzene sulfonyl chloride. Accordingly the third intermediate may be more generally represented by the formula:

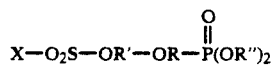

wherein X is selected from the group consisting of

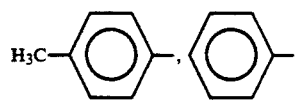

and alkyl groups having from about 1 to 6 carbon atoms. In addition to their utility in the production of the polyether bis-phosphonic acid compounds of this invention, these third intermediate esters can themselves be hydrolyzed to phosphonic acids and water soluble salts thereof which are considered useful in water treatment as corrosion and/or scale inhibitors. It is noted that the sulfonate group (whether toluene sulfonate, benzene sulfonate, or alkyl sulfonate) may also be removed during such hydrolysis.

The tetraalkyl alkyleneglycol di-(phosphonoalkyl) ether produced in step (d) may generally be purified by dilution with diethyl ether, filtration through celite, and concentration under vacuum. The esters themselves are considered useful as flame retardants. However, we prefer to use this purified material for production of the corresponding polyether bis-phosphonic acids and their water soluble salts, which are corrosion inhibiting agents. The ethyleneglycol di-(phosphonomethyl) ether may generally be purified, if desired, by ion exchange chromatography.

The 2-benzyloxyalkyl p-toluenesulfonate used in step (a) may be prepared by conventional techniques from commercially available material. For example, a solution of 2-benzyloxyethanol and toluene sulfonyl chloride may be added to a slurry of sodium hydride in ethylene glycol dimethyl ether cooled (e.g. using an ice bath) under a nitrogen atmosphere. After the addition, the mixture is warmed and allowed to react at room temperature. Crude 2-benzyloxyethyl p-toluenesulfonate may be obtained from the reaction mixture by diluting the mixture with diethyl ether, filtering the diluted mixture through anhydrous magnesium sulfate, and concentrating the filtered product under vacuum.

An alternative method of preparing the 2-benzyloxyalkyl p-toluenesulfonate involves adding pyridine or triethylamine to a cooled solution of 2-benzyloxyethanol and toluene sulfonyl chloride in dichloromethane under a nitrogen atmosphere; warming the mixture and allowing it to react at room temperature; washing the reacted mixture with dilute hydrochloric acid, sodium bicarbonate solution, and then with brine; drying the washed product over anhydrous magnesium sulfate; filtering; and concentrating the filtered product under vacuum.

It is considered that the 2-benzyloxyalkyl p-toluenesulfonate may be replaced in step (a) by other reactants such as 2-benzyloxyalkyl benzenesulfonate and 2-benzyloxyalkyl alkylsulfonate wherein the alkylsulfonate group has from from about 1 to 6 carbon atoms. The benzenesulfonate may be prepared by substituting benzene sulfonyl chloride for the toluene sulfonyl chloride in the above syntheses; and the alkylsulfonate may be prepared by substituting an alkane sulfonyl chloride for the toluene sulfonyl chloride. In any case, as suggested above, the benzene ring of the 2-benzyloxyalkyl alcohol, may optionally be substituted with one or more substituents selected from the group consisting of halogen groups, alkyl groups having from about 1 to 30 carbon atoms, and alkoxy groups having from about 1 to 30 carbon atoms, so that the resultant sulfonate used in step (a) may be correspondingly substituted as desired.

A method of preparing the bisphosphonic acid compounds of this invention where n is 2, 3, or 4 involves reacting a hydroxyalkyl phosphonic acid dialkyl ester compound of the above-referenced formula with a dihalogenated ether of the formula X—R'—(O—R')$_{n-1}$—X, where R' and n are as recited above, and X is selected from the group consisting of chlorine, bromine, and iodine, to form the respective tetraalkyl ester of the bis-phosphonic acid ether. The reaction is suitably accomplished by adding a solution of the hydroxyalkyl phosphonic acid dialkyl ester and the dihalogenated ether in a solvent such as ethylene glycol dimethyl ether to a slurry of sodium hydride in said solvent under an inert atmosphere such as nitrogen or argon. The bisphosphonic acid ether may be produced by dissolving its tetraalkyl ester in a concentrated acid such as hydrochloric acid and refluxing the acid solution.

Accordingly, the compound

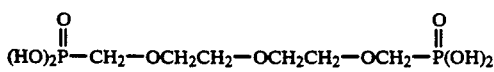

(i.e., each R is methylene, each R' is ethylene, and n is 2) may be conveniently prepared by adding a solution of the diethyl ester of hydroxymethylphosphonic acid and bis-(2-bromoethyl) ether (i.e. BrCH$_2$CH$_2$—O—CH$_2$CH$_2$Br) to a slurry of sodium hydride in ethylene glycol dimethyl ether under a nitrogen atmosphere, thereby forming tetraethyl bis-(2-phosphonomethoxyethyl) ether. The tetraethyl bis-(2-phosphonomethoxyethyl) ether may be dissolved in concentrated hydrochloric acid and the resulting solution refluxed to yield bis-(2-phosphonomethoxyethyl) ether.

The tetraethyl bis-(2-phosphonomethoxyethyl) ether may be purified by dilution with diethyl ether, and filtration through celite, followed by silica gel chromatography. The esters themselves are considered useful as flame retardants. We prefer to use this purified material for production of the corresponding polyether bis-phosphonic acids and their water soluble salts. The bis-(2-phosphonomethyoxyethyl) ether is concentrated under vacuum to remove hydrochloric acid, and may be substantially purified, if desired by ion exchange chromatography. However the unpurified product is itself considered useful as a corrosion inhibitor, and typically includes minor amounts of other materials such as hydroxymethyl phosphonic acid which is considered not to interfere with the effectiveness of the product and may even contribute to the product's corrosion inhibiting effectiveness under certain circumstances.

The triethylene glycol diphosphonomethyl ether compounds (i.e. n=3) and tetraethylene glycol diphosphonomethyl ether (i.e. n=4) compounds may be produced using basically the same procedure used in producing the bis-(2-phosphono-methoxyethyl) ether compounds, except that the corresponding dihalogenated ethers are used instead as reactants. The corresponding bis-(2-phosphonoethoxyethyl) ether compounds, triethylene glycol diphosphonoethyl ether compounds, and tetraethylene glycol diphosphonoethyl ether compounds (i.e. R is ethylene) may be produced using basically the same procedure used in producing the bis-(2-phosphonomethoxyethyl) ether compounds, except that a dialkyl ester of hydroxyethylphosphonic acid is used as a reactant instead of the diethyl ester of hydroxymethylphosphonic acid, and, as appropriate, the corresponding dihalogenated ethers are employed. It will be evident that other polyether bis-phosphonic acid compounds of the invention where n is 2, 3, or 4 may be produced in a similar manner using the appropriate dihalogenated ethers and, the appropriate hydroxyalkylphosphonic acid dialkyl ester reactants.

Salts of the bis-phosphonic acids of this invention may be straightforwardly produced by neutralizing the acid with the appropriate base. While esters may be produced as described above, they may also be prepared from the bis-phosphonic acids through conventional phosphonic acid esterification techniques (See, for example D. A. Nicholson et al., Journal of Organic Chemistry, 35, 3149 (1970).

Practice of the invention will become further apparent from the following non-limiting examples:

EXAMPLE I

To a slurry of sodium hydride (0.4 g, 17 mmol) in 20 ml ethylene glycol dimethyl ether cooled with an ice bath under an atmosphere of nitrogen, a solution of 2-benzyloxyethanol (2.1 ml, 15 mmol) and p-toluene sulfonyl chloride (2.9 g, 15 mmol) in ethylene glycol dimethyl ether was added dropwise. When the addition was complete, the ice bath was removed and the solution stirred at room temperature for 18 hours. After dilution with diethyl ether, the resulting slurry was filtered through anhydrous magnesium sulfate and concentrated under vacuum to yield 3.6 g of crude 2-benzyloxyethyl p-toluenesulfonate.

EXAMPLE II

Crude 2-benzyloxyethyl p-toluenesulfonate prepared in accordance with the process of Example I above (3.6 g, 12 mmol) was dissolved in 20 ml ethylene glycol dimethyl ether together with diethyl hydroxymethylphosphonate (1.65 g, 10 mmol). The resulting solution was added dropwise to a slurry of sodium hydride (0.4 g, 17 mmol) in 20 ml ethylene glycol dimethyl ether at 0° C. under a nitrogen atmosphere. The reaction mixture was allowed to warm to room temperature and stirred for 3.5 days. The mixture was diluted with diethyl ether, filtered through magnesium sulfate and concentrated under vacuum to give 2.5 g of a clear liquid. Purification by silica gel chromatography gave 1.0 g of diethyl 2-(benzyloxy)ethoxymethylphosphonate.

EXAMPLE III

Palladium on carbon (10%, 100 mg) was added to a solution of diethyl 2-(benzyloxy)ethoxymethylphosphonate prepared in accordance with the process of Example II above (0.9 g, 2.8 mmol) and cyclohexene (2.0 ml, 20 mmol) in 20 ml ethanol under a nitrogen atmosphere. The resulting slurry was heated to reflux overnight. The catalyst was filtered off and the solution concentrated under vacuum to yield 0.5 g of diethyl 2-hydroxyethoxymethylphosphonate.

EXAMPLE IV

Diethyl 2-hydroxyethoxymethylphosphonate prepared in accordance with the process of Example III above (2.5 g, 12 mmol) was dissolved in 13 ml dichloromethane under a nitrogen atmosphere. p-Toluenesulfonyl chloride (2.7 g, 14 mmol) was added and a solution of pyridine (2.3 ml, 28 mmol) in 7 ml dichloromethane was added dropwise. After stirring for three days at room temperature, the mixture was diluted with dichloromethane and washed successively with water, 1N hydrochloric acid, 5% sodium bicarbonate and saturated sodium chloride. After drying over anhydrous magnesium sulfate, the organic phase was concentrated under vacuum to yield 3.3 g of a cloudy liquid. Purification by silica gel chromatography yielded 0.7 g of diethyl 2-(phosphonomethoxy)ethyl p-toluene sulfonate.

EXAMPLE V

Diethyl 2-(phosphonomethoxy)ethyl p-toluene sulfonate preapared in accordance with the process of Example IV above (0.5 g, 1.4 mmol) was dissolved in 5 ml ethylene glycol dimethyl ether together with diethyl hydroxymethylphosphonate (0.3 g, 2 mmol). This solution was added dropwise to an ice cooled slurry of sodium hydride (0.06 g, 2 mmol) in 5 ml ethylene glycol dimethyl ether under a nitrogen atmosphere. The mixture was stirred at room temperature for 25 hours, refluxed for 4.5 hours and stirred another 19.5 hours at room temperature. During this period of time an additional 1.0 mmol diethyl hydroxymethylphosphonate and 0.09 g sodium hydride were introduced into the reaction. The mixture was then diluted with diethyl ether, filtered through celite and concentrated under vacuum to give 0.3 g of crude tetraethyl ethyleneglycol di-(phosphonomethyl) ether.

EXAMPLE VI

A solution of the tetraethylethyleneglycol di-(phosphonomethyl) ether prepared in accordance with the process of Example V (1.2 g, 3.3 mmol) in 15 ml concentrated hydrochloric acid was heated to reflux for 3 hours. An additional 5 ml of acid was added and the reflux continued for another 7.5 hours. After standing overnight at room temperature, the solution was concentrated under vacuum. The residue was dissolved in water and washed with hexane. Concentration under vacuum gave 0.6 g of ethyleneglycol di-(phosphonomethyl) ether. The structure of the ethyleneglycol di-(phosphonomethyl) ether was verified by nuclear magnetic resonance spectroscopy (carbon-13, proton, and phosphorous) as well as fast atom bombardment mass spectrometry.

EXAMPLE VII

Sodium hydride (0.24 g, 10 mmol) was slurried in 8 ml ethylene glycol dimethyl ether under a nitrogen atmosphere. The reaction was cooled with an ice bath and a solution of bis-(2-bromoethyl) ether (1.0 g, 4.0 mmol) and diethyl hydroxymethylphosphonate (1.5, 8.0 mmol) in 7 ml ethylene glycol dimethyl ether was added dropwise. Upon completion of the addition, the ice bath was removed and the reaction allowed to stir at room temperature for 3.5 hours. At this point another 0.2 g (1 mmol) of the diethyl phosphonate and 0.05 g (2 mmol) of sodium hydride were added. After stirring for another 18.5 hours at room temperature, the reaction was diluted with ether and filtered through celite. The solution was concentrated and purified on a silica gel column to give 0.5 g of tetraethyl bis-(2-phosphonomethoxyethyl) ether.

EXAMPLE VIII

A solution of 4.1 g (10 mmol) of tetraethyl bis-(2-phosphonomethoxyethyl) ether prepared in accordance with the process of Example VII above in 15 ml concentrated hydrochloric acid (conc. HCl) was heated to reflux for 3.5 hours. Another 15 ml of concentrated HCl was added and the solution refluxed another 2.0 hours. After standing overnight at room temperature, the mixture was refluxed an additional 3.0 hours. It was then concentrated under vacuum and dried in a vacuum oven at 80° C. for three days to yield 2.9 g of a viscous oil. Examination by nuclear magnetic resonance spectroscopy (carbon-13, proton, and phosphorous) showed the product to be the desired bis-(2-phosphonomethoxyethyl) ether, contaminated with 10% hydroxymethylphosphonic acid. The molecular weight of the product was confirmed by fast atom bombardment mass spectrometry.

The utility of the polyether bis-phosphonic acid compounds of this invention will become further apparent from the following. A standard corrosive test water solution containing 30 milligrams per liter (mg/l) calcium chloride, 37 mg/l magnesium sulfate, 100 mg/l sodium sulfate, 50 mg/l sodium chloride and 100 mg/l sodium carbonate was prepared by adding the recited salts to distilled water. The solution was thus free of such materials as chromate, zinc, phosphate, polyphosphate, nitrite, nitrate and borate. The test solution was added to a simulated cooling water test rig having a 12 liter reservoir and a recirculation loop. The rig generally corresponded in design with that described in The Development and Use of Corrosion Inhibitors, A. Marshall and B. Greaves, Oyez, London (1983). Four precleaned and preweighed mild steel metal test coupons were immersed in the test solution within the recirculating loop, and a fifth coupon was immersed in the test solution in the reservoir. The test solution in the rig was maintained at a temperature of about 55° C., and the pH was adjusted to about 8.5 as the test began. The recirculating flow (generally about 9 liters/min) produced a water velocity of approximately 1.6 feet/sec. past the coupons in the recirculation line while the water in the reservoir was substantially quiescent.

Two of the coupons in the recirculation line were removed after only 24 hours, and the remaining coupons were removed after 48 hours. The coupons were cleaned after removal and reweighed to determine weight loss. An average corrosion rate in mils (thousandths of an inch) per year was then calculated for the four recirculation line coupons, and a corrosion rate in mils per year was separately calculated for the reservoir coupon. The corrosion rates for the standard corrosive test water solution were calculated as 186 mils per year for the recirculation line coupons and 72 mils per year for the reservoir coupon.

A second run (run b) was made using the same procedure except that 15 ppm of ethyleneglycol di-(phosphonomethyl) ether (i.e. "EDPME"), prepared generally in accordance with the procedure illustrated above, was added to the standard corrosive test water solution. The corrosion rates for the recirculation line coupons and reservoir coupon were calculated. The percent corrosion inhibition compared to the run using only the standard corrosive test water (run a) is shown in Table A.

Additional runs (runs c, d and e) respectively using EDPME at concentrations of 22 ppm, 25 ppm and 38 ppm were also made and the percent corrosion inhibition compared to the run using only the standard corrosive test water is shown in Table A.

For comparison, hydroxymethylphosphonic acid (i.e. "HMPA") was synthesized by conventional means from phosphorous acid and formaldehyde (See U.K. Patent Specification No. 1,076,244), and was tested in a series of 8 runs (runs f through m). The percent corrosion inhibition using HMPA at 30 ppm (runs f and g), 50 ppm (run h), 100 ppm (runs i, j and k) and 200 ppm (runs l and m) is shown in Table A.

A series of three runs (runs n through p) was made using equal amounts of EDPME and HMPA (10 ppm, 15 ppm and 20 ppm each respectively for the three runs). The percent corrosion inhibition compared to run a is shown in Table A.

A series of 3 runs (runs q through s) was made using a mixture of HMPA and bis-(2-phosphonomethoxyethyl) ether (i.e. "BPMEE") prepared generally in accordance with the procedure illustrated above, as the corrosion inhibitor. The mixture had a weight ratio of HMPA to BPMEE of about 1:9. The percent corrosion inhibitor using a total concentration of both compounds of 24 ppm (run q), 36 ppm (run r), and 47 ppm (run s) is shown in Table A.

TABLE A

| Run No. | Corrosion Inhibitor | Inhibitor Dosage (ppm) | Percent Reduction in Corrosion Rate | |
|---|---|---|---|---|
| | | | Recirculation Line | Reservoir |
| a | None | 0 | 0 (Base Rate) | 0 (Base Rate) |
| b | EDPME | 15 | 70 | 35 |
| c | EDPME | 22 | 85 | 19 |
| d | EDPME | 25 | 90 | 32 |
| e | EDPME | 38 | 99 | 98 |
| f | HMPA | 30 | 49 | 43 |
| g | HMPA | 30 | 46 | 41 |
| h | HMPA | 50 | 72 | 26 |
| i | HMPA | 100 | 96 | 56 |
| j | HMPA | 100 | 93 | 37 |
| k | HMPA | 100 | 94 | 43 |
| l | HMPA | 200 | 99 | 62 |
| m | HMPA | 200 | 98 | 75 |
| n | EDPME/HMPA(1:1) | 20 | 66 | 39 |
| o | EDPME/HMPA(1:1) | 30 | 94 | 42 |
| p | EDPME/HMPA(1:1) | 40 | 95 | 44 |
| q | BPMEE/HMPA(9:1) | 24 | 60 | 22 |
| r | BPMEE/HMPA(9:1) | 36 | 97 | 17 |
| s | BPMEE/HMPA(9:1) | 47 | 96 | 71 |

The Examples describe particular embodiments of the invention. Other embodiments will become apparent to those skilled in the art from a consideration of the specification or practice of the invention disclosed herein. It is understood that modifications and variations may be produced without departing from the spirit and scope of the novel concepts of this invention. It is further understood that the invention is not confined to the particular formulations and examples herein illustrated, but it embraces such modified forms thereof as come within the scope of the following claims.

What is claimed is:

1. A compound of the formula

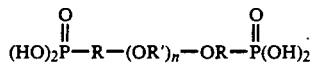

where R is —$CH_2$—, R' is selected from the group consisting of —$CH_2CH_2$—, and —$CH_2CH_2$— which is substituted with one or more methyl groups, and n is an integer from 1 to 4, water soluble salts thereof, and esters thereof with alkyl groups having from 1 to 6 carbon atoms.

2. A compound according to claim 1 wherein the compound is a polyether bis-phosphonic acid or a water soluble salt thereof.

3. A compound according to claim 2 wherein R' is ethylene.

4. A compound according to claim 2 wherein n is 1.

5. A compound according to claim 2 wherein R' is ethylene and n is 1.

6. A compound according to claim 2 wherein R' is ethylene and n is 2.

* * * * *